(12) United States Patent
Pullagurla et al.

(10) Patent No.: US 12,227,527 B2
(45) Date of Patent: Feb. 18, 2025

(54) PROCESS FOR THE PREPARATION OF 2,2',2''-(10-((2R,3S)-1,3,4-TRIHYDROXY BUTAN-2-YL)-1,4,7,10-TETRAAZACYCLO-DODECANE-1,4,7-TRIYL) TRIACETIC ACID AND ITS COMPLEXES

(71) Applicant: BIOPHORE INDIA PHARMACEUTICALS PVT. LTD, Hyderabad (IN)

(72) Inventors: Manik Reddy Pullagurla, Hyderabad (IN); Jagadeesh Babu Rangisetty, Hyderabad (IN); Bhaskar Reddy Pitta, Hyderabad (IN)

(73) Assignee: BIOPHORE INDIA PHARMACEUTICALS PVT. LTD, Hyderabad (IN)

( * ) Notice: Subject to any disclaimer, the term of this patent is extended or adjusted under 35 U.S.C. 154(b) by 0 days.

(21) Appl. No.: 17/258,890

(22) PCT Filed: Jul. 10, 2019

(86) PCT No.: PCT/IB2019/055868
§ 371 (c)(1),
(2) Date: Jan. 8, 2021

(87) PCT Pub. No.: WO2020/012372
PCT Pub. Date: Jan. 16, 2020

(65) Prior Publication Data
US 2021/0284662 A1    Sep. 16, 2021

(30) Foreign Application Priority Data

Jul. 10, 2018 (IN) .............................. 201841025736
Jul. 12, 2018 (IN) .............................. 201841026063

(51) Int. Cl.
| C07F 5/00 | (2006.01) |
| C07B 63/04 | (2006.01) |
| C07F 3/00 | (2006.01) |

(52) U.S. Cl.
CPC .............. *C07F 5/003* (2013.01); *C07B 63/04* (2013.01); *C07F 3/003* (2013.01); *C07B 2200/13* (2013.01)

(58) Field of Classification Search
CPC .................... C07F 5/003; C07F 3/04
See application file for complete search history.

(56) References Cited

U.S. PATENT DOCUMENTS

| 5,386,028 A * | 1/1995 | Tilstam ................. C07D 257/02 540/452 |
| 5,410,043 A * | 4/1995 | Platzek ................. C07D 257/02 340/474 |

(Continued)

FOREIGN PATENT DOCUMENTS

| CN | 102399199 A * | 4/2012 |
| CN | 103613557 A | 3/2014 |

(Continued)

OTHER PUBLICATIONS

A. Sunil et al., Organic and Medicinal Chemistry, 1-4 (2018) (Year: 2018).*
H. Engelhardt, Quantitative Analysis in HPLC, in Practice of High Performance Liquid Chromatography Applications, Equipment and Quantitative Analysis, 65-108 (H. Engelhardt ed., 1985) (Year: 1985).*

(Continued)

*Primary Examiner* — Alexander R Pagano
(74) *Attorney, Agent, or Firm* — McCormick, Paulding & Huber PLLC

(57) ABSTRACT

The present invention relates to an improved process for the preparation of 2,2',2''-(10-((2R,3S)-1,3,4-trihydroxy butan-2-yl)-1,4,7,10-tetraazacyclododecane-1,4,7-triyl) triacetic acid, gadolinium (III) with iron metal content less than 5 ppm and free gadolinium content less than 10 ppm, which is represented by the formula (1). The present invention further relates to an improved process for the preparation of calcium complex of 10-(2,3-Dihydroxy-1-(hydroxymethyl)propyl)-1,4,7,10-tetraazacyclo decane-1,4,7-triacetic acid known as Calcobutrol (1a) and its sodium salt of formula (1b) with purity greater than 98.0%.

(1)

(1a)

(Continued)

-continued

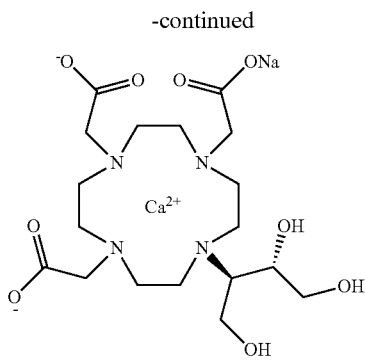

(1b)

5 Claims, 3 Drawing Sheets

(56) References Cited

U.S. PATENT DOCUMENTS

| | | | | |
|---|---|---|---|---|
| 5,595,714 | A | * | 1/1997 | Ripa ................ C01F 17/17 423/21.5 |
| 5,980,864 | A | | 11/1999 | Platzek et al. |
| 5,994,536 | A | * | 11/1999 | Petrov ............. C07D 257/02 540/450 |
| 6,042,810 | A | * | 3/2000 | Ripa ................ C07D 257/02 540/465 |
| 6,066,259 | A | * | 5/2000 | Viscardi .......... B01J 39/07 210/685 |
| 9,447,053 | B2 | | 9/2016 | Platzek |
| 2006/0078503 | A1 | * | 4/2006 | Platzek ............ C07D 257/02 424/9.363 |
| 2018/0105537 | A1 | | 4/2018 | Platzek et al. |

FOREIGN PATENT DOCUMENTS

| | | | | |
|---|---|---|---|---|
| WO | WO2011054827 | * | 11/2010 | ......... C07D 257/02 |
| WO | 2012143355 A1 | | 10/2012 | |
| WO | WO-2018059914 A1 | * | 4/2018 | ......... A61K 49/108 |

OTHER PUBLICATIONS

N. G. Anderson, Practical Process & Research Development, 113-143, 203-267 (2000) (Year: 2000).*

J. March, Advanced Organic Chemistry Reactions, Mechanisms and Structure 248-272 (4th ed., 1992) (Year: 1992).*

J. Qi et al., 19 Chemistry, a European Journal, 4146-4150 (2013) (Year: 2013).*

International Search Report for PCT/IB2019/055868 dated Oct. 16, 2019.

J. Platzek et al., "Synthesis and Structure of a New Macrocyclic Polyhydroxylated Gadolinium Chelate Used as a Contrast Agent for Magnetic Resonance Imaging," Inorganic chemistry, 1997, 36, pp. 6086-6093.

* cited by examiner

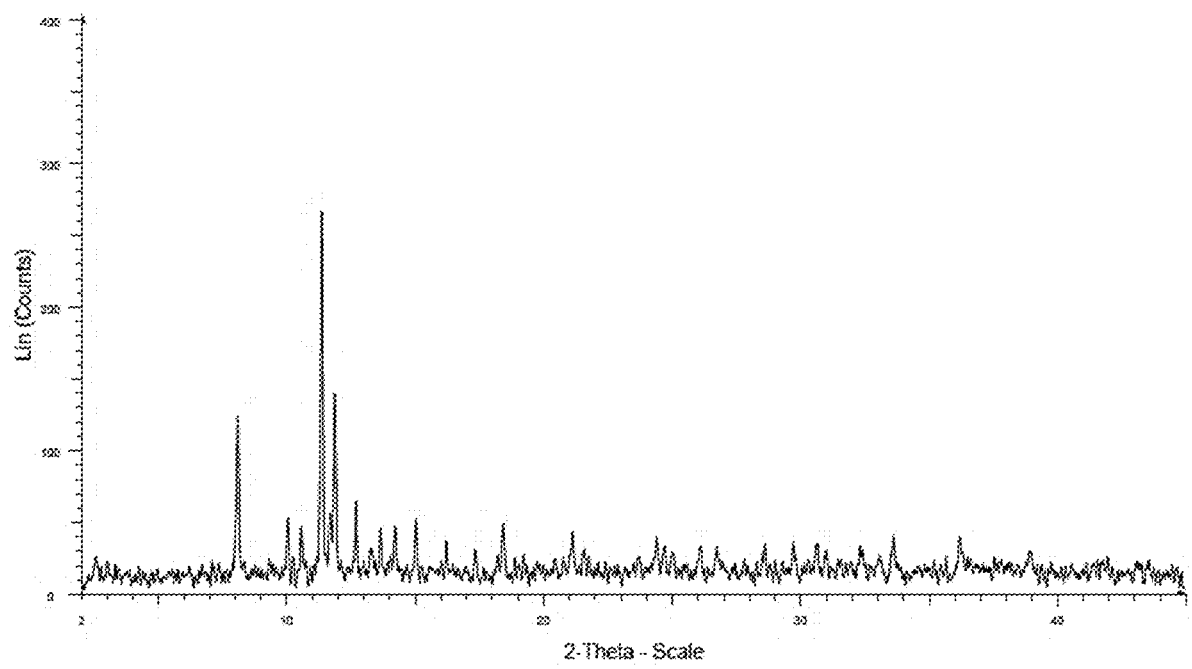
Figure-1: Illustrates the X-ray-powder diffraction pattern (XRPD) of Gadobutrol of formula (1)

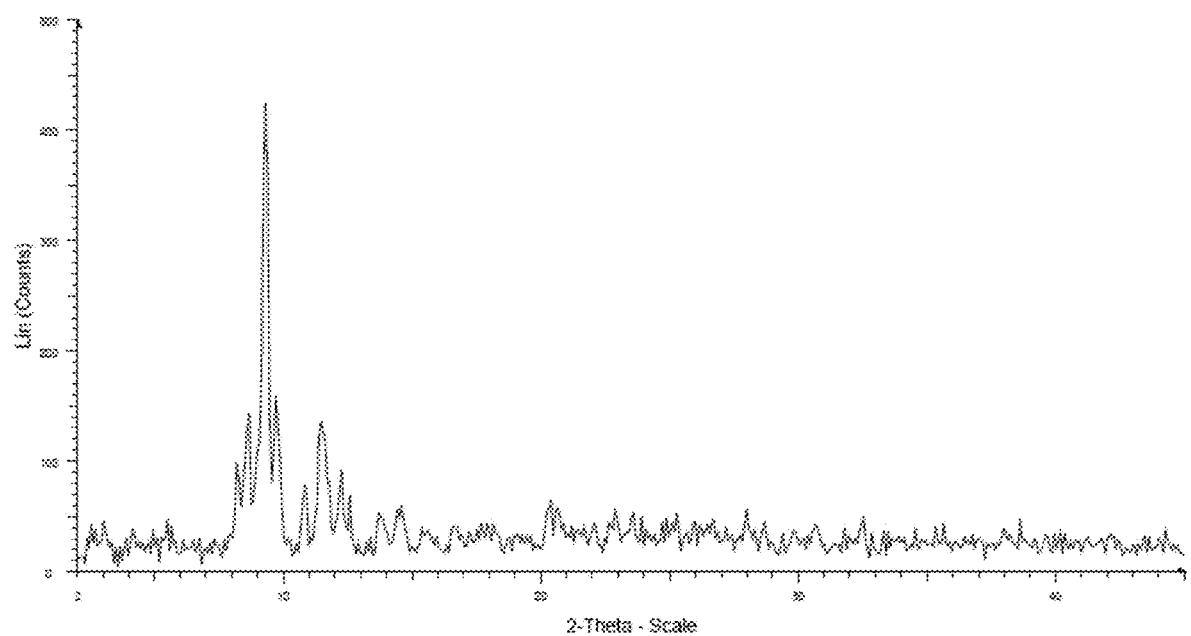
Figure-2: Illustrates the X-ray-powder diffraction pattern (XRPD) of Calcobutrol of formula (1a)

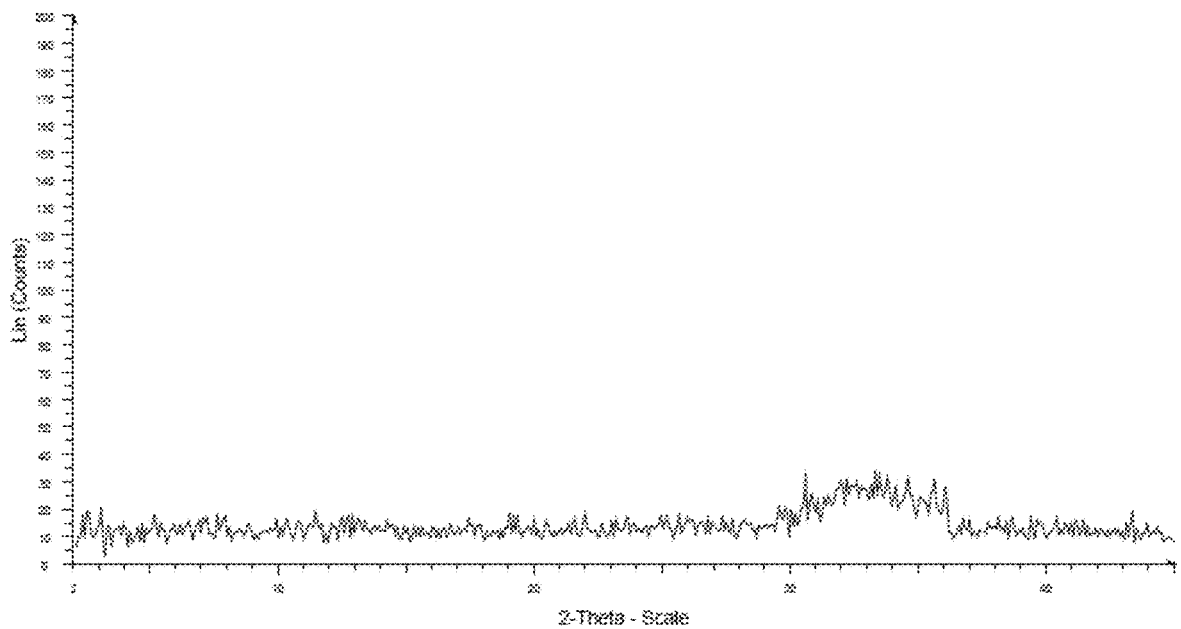
Figure-3: Illustrates the X-ray-powder diffraction pattern (XRPD) of Sodium salt of Calcobutrol of formula (1b)

PROCESS FOR THE PREPARATION OF 2,2',2''-(10-((2R,3S)-1,3,4-TRIHYDROXY BUTAN-2-YL)-1,4,7,10-TETRAAZACYCLO-DODECANE-1,4,7-TRIYL) TRIACETIC ACID AND ITS COMPLEXES

CROSS REFERENCE TO RELATED APPLICATIONS

This application is a National Stage application of International Patent Application No. PCT/IB2019/055868, filed on Jul. 10, 2019, which claims the priority from Indian Patent Application No. 201841025736 filed Indian Patent Office on Jul. 10, 2018 and Indian Patent Application No. 201841026063 filed Indian Patent Office on Jul. 12, 2018, each of which is hereby incorporated by reference in its entirety.

TECHNICAL FIELD

The present invention relates to an improved process for the preparation of 2,2',2''-(10-((2R,3S)-1,3,4-trihydroxybutan-2-yl)-1,4,7,10-tetraazacyclododecane-1,4,7-triyl) triacetic acid, gadolinium (III) with purity greater than 99.0% which is represented by the formula (1). It further relates to an improved process for the preparation of calcium complex of 10-(2,3-Dihydroxy-1-(hydroxymethyl)propyl)-1,4,7,10-tetraazacyclo decane-1,4,7-triacetic acid known as Calcobutrol of formula (1a) and its sodium salt of formula (1b) with purity greater than 98.0%.

BACKGROUND

Gadobutrol is a paramagnetic contrast agent indicated for intravenous use in diagnostic magnetic resonance imaging (MRI) to detect and visualize areas with disrupted blood brain barrier (BBB) and/or abnormal vascularity of the central nervous system. It is chemically known as 2,2',2''-(10-((2R,3S)-1,3,4-trihydroxybutan-2-yl)-1,4,7,10-tetraazacyclododecane-1,4,7-triyl) triacetic acid, gadolinium (III) salt. Gadobutrol is marketed under the proprietary name Gadovist by Bayer Healthcare Pharmaceuticals Inc. Calcobutrol is a calcium salt of butrol ligand, used as an additive in the formulation of Gadovist to stabilize the Gadolinium complex and to prevent the release of toxic Gadolinium ion into the solution. Calcobutrol is chemically known as calcium complex of 10-(2,3-Dihydroxy-1-(hydroxymethyl)propyl)-1,4,7,10-tetraazacyclodecane-1,4,7-triacetic acid.

U.S. Pat. No. 5,980,864 (herein after referred as US'864) discloses Gadobutrol (1) and its process for preparation, which involves reaction of 1,4,7-triscarboxymethyl-1,4,7,10 tetraazacyclododecane (DO3A) (IV) with 2-(2,2-dimethyl-1,3-dioxolan-4-yl)-ethylene oxide of formula (III) in presence of sodium hydroxide in 1,4-dioxane to yield 10-(2,3,4-Trihydroxybutyl)-1,4,7-triscarboxymethyl-1,4,7,10-tetraaza cyclo dodecane of formula (II). The obtained intermediate of formula (9) was converted to Gadobutrol of formula (I) by treating with gadolinium oxide in de-ionised water. US'864 patent does not disclose the purity of Gadobutrol of formula (I).

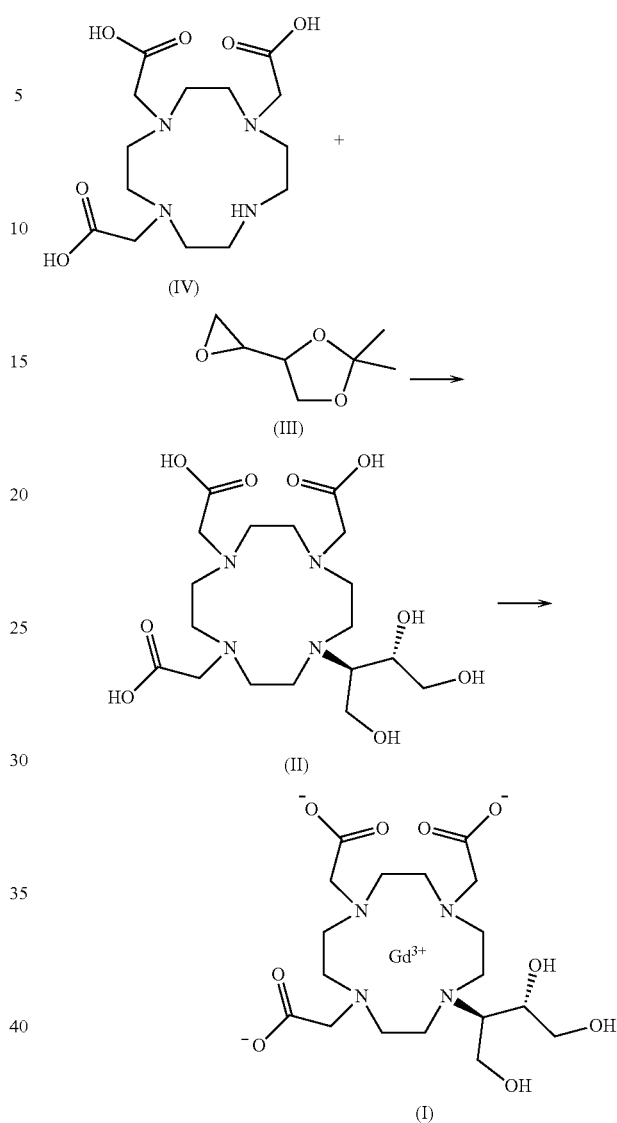

WO2012143355 application discloses the process for the preparation of Gadobutrol (I) consisting of reacting cyclen (1,4,7,10-tetraazacyclododecane) of formula (V) with 4,4-dimethyl-3,5,8-trioxabicyclo [5, 1, 0] octane of formula (VI) in isopropyl alcohol to yield intermediate of formula (VII), alkylation of intermediate of formula (VII) with sodium monochloroacetate of formula (VIII) in presence of sodium hydroxide provides intermediate of formula (II), converting intermediate of formula (9) to Gadobutrol of formula (I) by treating with gadolinium oxide in water in one pot fashion.

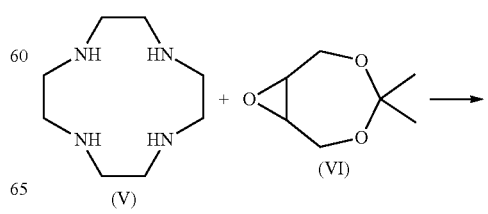

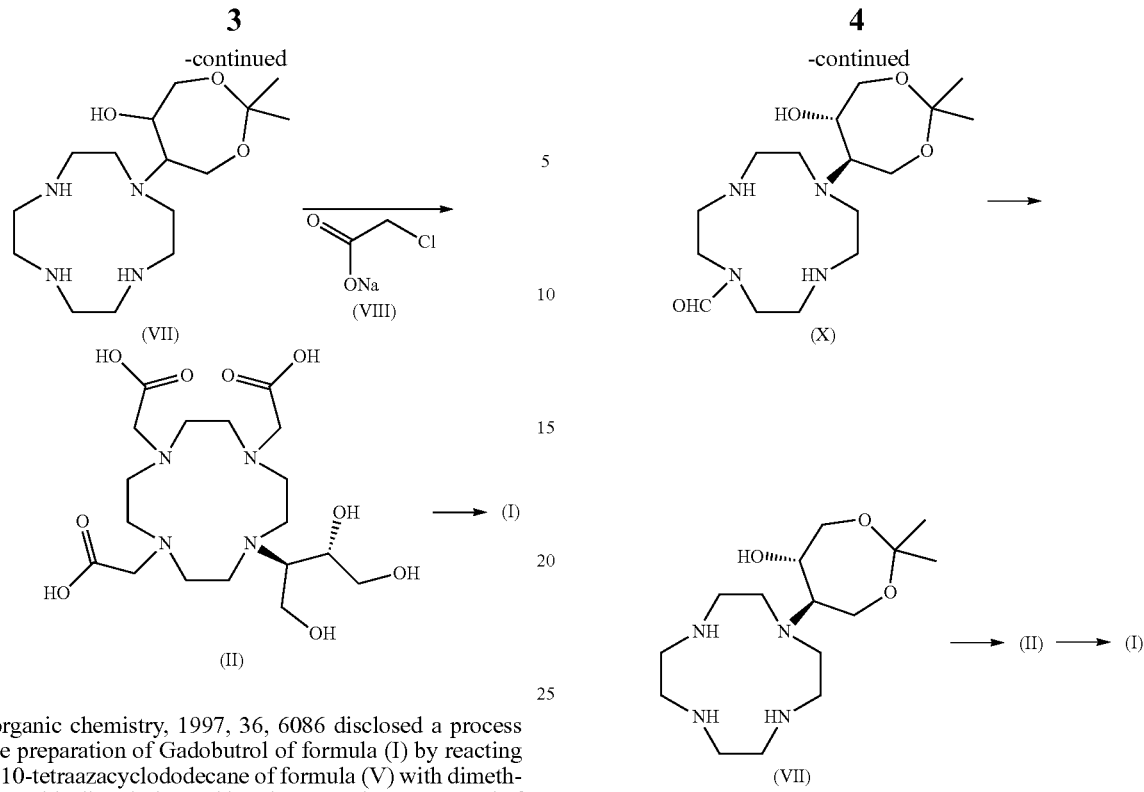

Inorganic chemistry, 1997, 36, 6086 disclosed a process for the preparation of Gadobutrol of formula (I) by reacting 1,4,7,10-tetraazacyclododecane of formula (V) with dimethylformamide dimethyl acetal in toluene to give compound of intermediate of formula (IX), which was reacted with 4,4-dimethyl-3,5,8-trioxabicyclo [5.1.0] octane followed by solvolysis with water-methanol (1:3) gave formyl derivative of formula (X). Alkaline treatment of intermediate of formula (X) removed the formyl group and resulted in the formation of the monosubstituted cyclen derivative of formula (VII), further alkylation of monosubstituted cyclen derivative with chloroacetic acid sodium salt in water gave the ligand DO3A-butrol of formula (II). The complexation of intermediate of formula (II) with gadolinium oxide in water furnished Gadobutrol of formula (I).

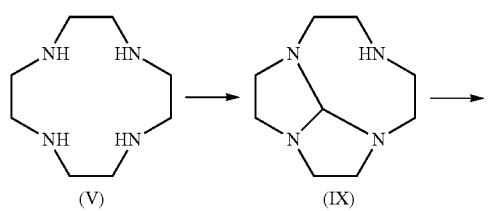

Based on importance of 2,2',2''-(10-((2R,3S)-1,3,4-trihydroxy butan-2-yl)-1,4,7,10-tetraazacyclo dodecane-1,4,7-triyl) triacetic acid, gadolinium (III) salt as an MRI diagnostic, it can be prepared by various routes.

U.S. Pat. No. 9,447,053 disclosed the process for the preparation of Calcobutrol of formula (Ia) from Gadobutrol of formula (I). The process involves decomplexation of Gadobutrol of formula (I) with an oxalic or phosphoric acid, followed by purification of obtained butrol ligand of formula (II) through ion exchange column, charcoal treatment and then reacted with calcium carbonate in water at a temperature of 90° C. It also discloses the preparation of sodium salt of Calcobutrol of formula (Ib) by reacting Calcobutrol of formula (Ia) with stoichiometric amount of sodium hydroxide.

-continued

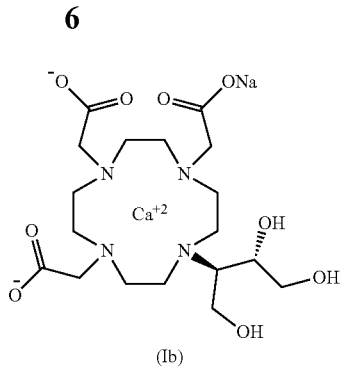

(Ib)

The prior art methods for the preparation of Gadobutrol of formula (I) were associated with some draw backs like lengthy processes involves multiple steps, require tedious and multiple purification processes by ion-exchange column chromatography to minimize the impurities formed in the reaction which may lead to loss of yield of the final product Gadobutrol of formula (I). Even though the final API Gadobutrol of formula (I) is devoid of impurities the process is not suitable for industrial scale sample.

Also, the prior art processes for the preparation of Calcobutrol of formula (Ia) have drawbacks like lengthy processes, use of sodium metal and maintaining lower temperatures which is not suitable for commercial scale purposes. Purification by silica-gel column chromatography, and multiple purification of butrol ligand makes the prior art processes tedious and difficult to handle at industrial level. Purification of butrol ligand is necessary otherwise traces of toxic Gadolinium metal will reside in the final compound.

To overcome these disadvantages in prior arts, the present inventors hereby provide an improved process for the preparation of pure Gadobutrol of formula (1), Calcobutrol of formula (1a) and sodium salt of Calcobutrol of formula (1b) which is feasible at industrial scale.

Accordingly, one objective of the present invention is to provide an improved process for the preparation of Gadobutrol of formula (1).

Another objective of the present invention is to provide a process for the purification of Gadobutrol of formula (1).

Another objective of the present invention is to provide Gadobutrol of formula (1) with purity greater than 99.0% by High-performance liquid chromatography (HPLC).

Another objective of the invention is to provide process to control impurities of Gadobutrol of formula (1) like 2,2'-(4-((2R,3S)-1,3,4-trihydroxybutan-2-yl)-10-((2S,3S)-1,3,4-trihydroxybutan-2-yl)-1,4,7,10-tetraazacyclododecane-1,7diyl)diacetic acid (di-TOBO) of formula (8), and 2,2',2'',2'''-(1,4,7,10-tetraazacyclododecane-1,4,7,10-tetrayl) tetraacetic acid (DOTA) of formula (9); 2,2',2''-(1,4,7,10-tetraazacyclododecane-1,4,7-triyl) triacetic acid, gadolinium (III) salt (10) and 2,2',2'',2'''-(1,4,7,10-tetraazacyclododecane-1,4,7,10-tetrayl)tetraacetic acid, gadolinium (III) salt (Gd-DOTA Impurity) (11) below 1.0% (w/w), preferably less than 0.5% (w/w).

Another objective of the present invention is to provide Gadobutrol of formula (1) with iron metal content less than 10 ppm, more preferably less than 5 ppm and still more preferably less than 2 ppm.

Yet, in another objective the present invention provides crystalline form of Gadobutrol of formula (1).

Another objective of the present invention is to provide a process for the preparation of Calcobutrol of formula (1a) and sodium salt of Calcobutrol of formula (1b) with purity greater than 98.0% by High performance liquid chromatography (HPLC).

Yet, in another objective the present invention provides crystalline form of Calcobutrol of formula (1a).

Yet still, in another objective, the present invention provides amorphous form of sodium salt of Calcobutrol of formula (1b).

SUMMARY

Accordingly, in one aspect the present invention provides a process for the preparation of Gadobutrol of formula (1) comprising:
a) reacting a compound 1,4,7,10-tetraazacyclododecane of formula (6) with compound 4,4-dimethyl-3,5,8-trioxabicyclo[5.1.0]octane of formula (5) to obtain a compound 2,2-dimethyl-6-(1,4,7,10-tetraazacyclododecan-1-yl)-1,3-dioxepan-5-ol of formula (4) in presence of suitable metal salt and acid;
b) reacting a compound 2,2-dimethyl-6-(1,4,7,10-tetraazacyclododecan-1-yl)-1,3-dioxepan-5-ol of formula (4) with a compound sodium 2-chloroacetate of formula (3) to provide a compound 2,2',2''-(10-((2R,3S)-1,3,4-trihydroxybutan-2-yl)-1,4,7,10-tetraazacyclododecane-1,4,7-triyl) triacetic acid, triammonium salt of formula (2) in presence of a suitable base; and
c) reacting a compound 2,2',2''-(10-((2R,3S)-1,3,4-trihydroxybutan-2-yl)-1,4,7,10-tetraaza cyclododecane-1,4,7-triyl) triacetic acid, triammonia salt of formula (2) with Gadolinium (III) oxide to yield 2,2',2''-(10-((2R,3S)-1,3,4-trihydroxybutan-2-yl)-1,4,7,10-tetraazacyclododecane-1,4,7-triyl) triacetic acid, gadolinium (III) salt of formula (1).
d) purifying Gadobutrol of formula (1) by treating with acidic resin and basic resins.

In another aspect, the present invention provides process for the purification of compound 2,2',2''-(10-((2R,3S)-1,3,4-trihydroxybutan-2-yl)-1,4,7,10-tetraazacyclo dodecane-1,4,7-triyl)triacetic acid, triammonia salt of formula (2) comprising:
I. providing a mixture of intermediate of formula (2) in a protic solvent;
II. adding suitable acidic resin to the reaction mixture;
III. treating the reaction mixture with suitable base; and
IV. isolating the pure intermediate of formula (2).

The present invention provides compound 2,2',2''-(10-((2R,3S)-1,3,4-trihydroxybutan-2-yl)-1,4,7,10-tetraazacyclododecane-1,4,7-triyl) triacetic acid, triammonia salt of formula (2) with purity greater than 90.0% which forms another embodiment of the invention.

Yet, in another aspect of the present invention provides a process for the purification of compound 2,2',2''-(10-((2R,3S)-1,3,4-trihydroxybutan-2-yl)-1,4,7,10-tetraazacyclo dodecane-1,4,7-triyl) triacetic acid, gadolinium (III) salt of formula (1) comprising:

a) providing a solution of Gadobutrol of formula (1) in a protic solvent;
b) treating the reaction mixture with acidic and basic resins;
c) optionally, treating the reaction mixture with activated carbon and;
d) isolating pure Gadobutrol of formula (1).

In another aspect the compound 2,2',2''-(10-((2R,3S)-1,3,4-trihydroxybutan-2-yl)-1,4,7,10-tetraazacyclo dodecane-1,4,7-triyl) triacetic acid, gadolinium (III) salt of formula (1) obtained after purification is having purity greater than 99.0% by HPLC.

In another aspect the present invention also provides a process for controlling the impurities like 2,2'-(4-((2R,3S)-1,3,4-trihydroxybutan-2-yl)-10-((2S,3S)-1,3,4-trihydroxybutan-2-yl)-1,4,7,10-tetraazacyclododecane-1,7diyl) diacetic acid (di-TOBO) of formula (8), and 2,2',2'',2'''-(1,4,7,10-tetraazacyclododecane-1,4,7,10-tetrayl) tetraacetic acid (DOTA) of formula (9); 2,2',2''-(1,4,7,10-tetraazacyclododecane-1,4,7-triyl) triacetic acid, gadolinium (III) salt of formula (10) and 2,2',2'',2'''-(1,4,7,10-tetraazacyclododecane-1,4,7,10-tetrayl)tetraacetic acid, gadolinium (III) salt (Gd-DOTA Impurity) of formula (11) below 1.0% (w/w), preferably less than 0.5% (w/w).

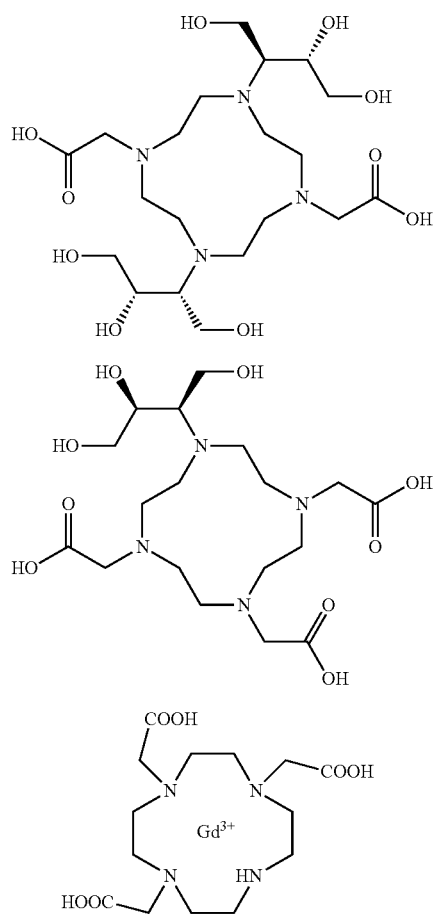

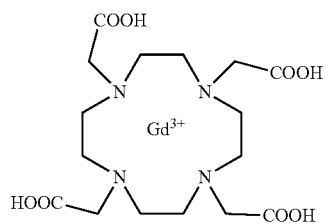

In another aspect the present invention also provides a process for controlling impurity 6,6'-(1,4,7,10-tetraazacyclododecane-1,7-diyl) bis(2,2-dimethyl-1,3-dioxepan-5-ol) of formula (12).

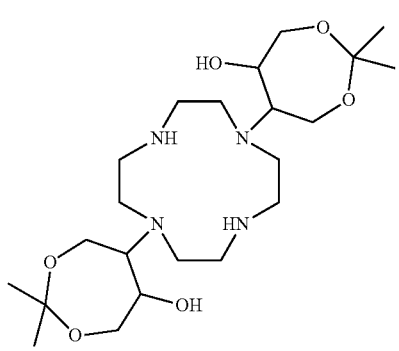

In another aspect the compound 2,2',2''-(10-((2R,3S)-1,3,4-trihydroxybutan-2-yl)-1,4,7,10-tetraazacyclo dodecane-1,4,7-triyl) triacetic acid, gadolinium (III) salt of formula (1) obtained after purification is having total Iron metal content less than 10 ppm, more preferably Iron metal content is less than 5 ppm.

In some aspect the present invention provides a process for the preparation of Calcobutrol of formula (1a) and its sodium salt of formula (1b) comprising:

a) reacting a compound 1,4,7,10-tetraazacyclododecane of formula (6) with compound 4,4-dimethyl-3,5,8-trioxabicyclo[5.1.0]octane of formula (5) to obtain a compound 2,2-dimethyl-6-(1,4,7,10-tetraazacyclododecan-1-yl)-1,3-dioxepan-5-ol of formula (4);
b) reacting a compound 2,2-dimethyl-6-(1,4,7,10-tetraazacyclododecan-1-yl)-1,3-dioxepan-5-ol (4) with a compound sodium 2-chloroacetate of formula (3) to provide a compound 2,2',2''-(10-((2R,3S)-1,3,4-trihydroxy butan-2-yl)-1,4,7,10-tetraazacyclododecane-1,4,7-triyl)triacetic acid of formula (7); and
c) reacting a compound 2,2',2''-(10-((2R,3S)-1,3,4-trihydroxybutan-2-yl)-1,4,7,10-tetraaza cyclododecane-1,4,7-triyl)triacetic acid of formula (7) with Calcium hydroxide to yield calcium 2,2'-(7-(carboxymethyl)-10-((2R,3S)-1,3,4-trihydroxybutan-2-yl)-1,4,7,10-tetraazacyclododecane-1,4-diyl)diacetate of formula (1a).
d) purifying Calcobutrol of formula (1a) from protic solvent or mixtures thereof.
e) converting calcium 2,2'-(7-(carboxymethyl)-10-((2R,3S)-1,3,4-trihydroxy butan-2-yl)-1,4,7,10-tetraazacyclododecane-1,4-diyl) diacetate of formula (1a) to sodium salt of calcium 2,2',2''-(10-((2R,3S)-1,3,4-trihydroxybutan-2-yl)-1,4,7,10-tetraazacyclododecane-1,4,7-triyl)triacetate of formula (1b) by treating with sodium hydroxide.

In another aspect the present invention provides a compound calcium 2,2'-(7-(carboxymethyl)-10-((2R,3S)-1,3,4-trihydroxybutan-2-yl)-1,4,7,10-tetraazacyclo dodecane-1,4-diyl) diacetate of formula (1a) and sodium salt of calcium 2,2',2"-(10-((2R,3S)-1,3,4-trihydroxybutan-2-yl)-1,4,7,10-tetraazacyclo dodecane-1,4,7-triyl)triacetate of formula (1b) with purity greater than 98.0% by HPLC.

In one aspect the pure Calcobutrol of formula (1a) and its sodium salt of formula (1b) obtained in the present invention were having impurities Calcium-DOTA impurity less than 2%, preferably less than 1%, and Calcium di-TOBO impurity than less than 1% preferably less than 0.5% and Calcium triacid impurity is less than 0.5% (w/w).

Yet still, in another aspect of the present invention is to provide a crystalline form of Calcobutrol of formula (1a).

In another aspect of the present invention is to provide an amorphous form of sodium salt of Calcobutrol of formula (1b).

BRIEF DESCRIPTION OF DRAWINGS

FIG. 1: illustrates the X-Ray powder diffraction pattern (XRPD) of Gadobutrol of formula (1).

FIG. 2: illustrates the X-Ray powder diffraction pattern (XRPD) of Calcobutrol of formula (1a).

FIG. 3: illustrates the X-Ray powder diffraction pattern (XRPD) of Sodium salt of Calcobutrol of formula (1b).

DETAILED DESCRIPTION

Accordingly, in one embodiment the present invention provides an improved process for the preparation of Gadobutrol of formula (1) with purity greater than 99.0% by HPLC.

Gadobutrol of formula (1) prepared in the present invention is as shown in scheme 1:

a) reacting a compound 1,4,7,10-tetraazacyclododecane of formula (6) with compound 4,4-dimethyl-3,5,8-trioxabicyclo[5.1.0]octane of formula (5) to obtain a compound 2,2-dimethyl-6-(1,4,7,10-tetraazacyclododecan-1-yl)-1,3-dioxepan-5-ol of formula (4) in presence of suitable metal salt and acid;

b) reacting a compound 2,2-dimethyl-6-(1,4,7,10-tetraazacyclododecan-1-yl)-1,3-dioxepan-5-ol of formula (4) with a compound sodium 2-chloroacetate of formula (3) to provide a compound 2,2',2"-(10-((2R,3S)-1,3,4-trihydroxybutan-2-yl)-1,4,7,10-tetraazacyclododecane-1,4,7-triyl) triacetic acid, triammonia salt of formula (2) in presence of a suitable base; and c) reacting a compound 2,2',2"-(10-((2R,3S)-1,3,4-trihydroxybutan-2-yl)-1,4,7,10-tetraaza cyclododecane-1,4,7-triyl) triacetic acid, triammonia salt of formula (2) with Gadolinium(III) oxide to yield 2,2',2"-(10-((2R,3S)-1,3,4-trihydroxybutan-2-yl)-1,4,7,10-tetraazacyclo dodecane-1,4,7-triyl) triacetic acid, gadolinium (III) salt of formula (1).

d) purifying Gadobutrol of formula (1) by treating with acidic resin and basic resins.

In some embodiment, step a) proceeds with reacting 1,4,7,10-tetraazacyclododecane of formula (6) with compound 4,4-dimethyl-3,5,8-trioxabicyclo [5.1.0] octane of formula (5) to form 2,2-dimethyl-6-(1,4,7,10-tetraazacyclododecan-1-yl)-1,3-dioxepan-5-ol of formula (4) in presence of suitable metal salt in a protic solvent and finally, isolated from an protic and aprotic solvents by adjusting the pH to 7-10, by adding suitable acid.

The suitable metal salt used in step a) can be selected from the group consisting of alkali metal salts, alkaline earth metal salts, transition metal salts or the like. Alkali metal salts were selected from the group comprising of lithium chloride, sodium chloride, potassium chloride or the like;

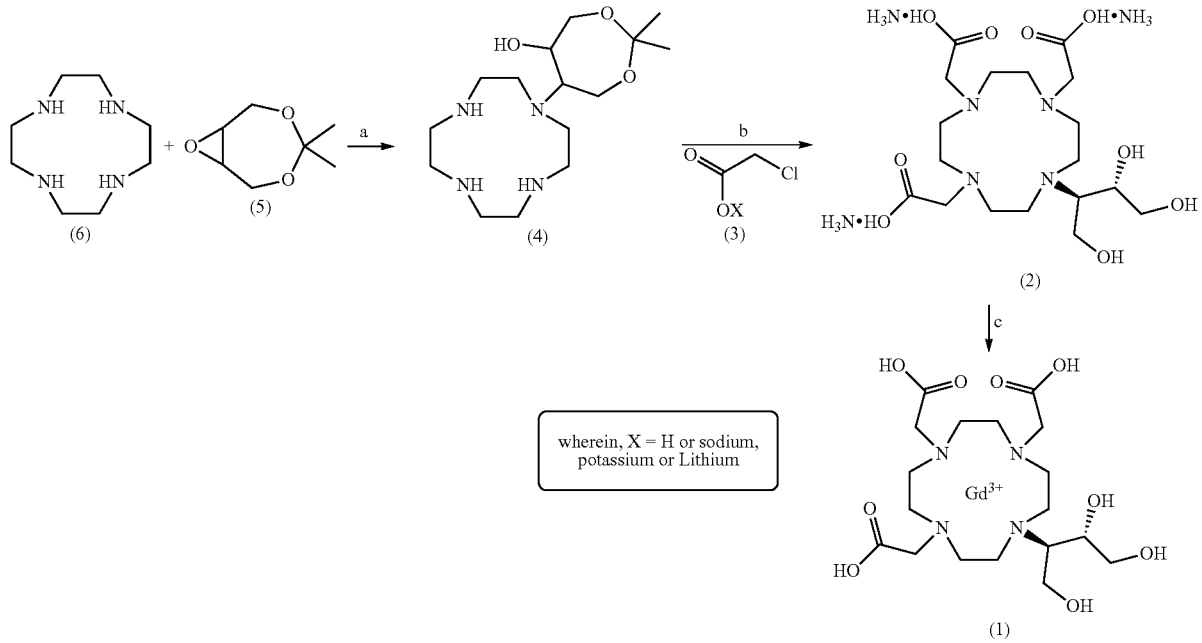

Scheme-1: Synthesis of Gadobutrol of Formula (1)

In some embodiment, the present invention relates to preparation of Gadobutrol of formula (1) comprising:

alkaline earth metal salts were selected from the group comprising of magnesium chloride, magnesium bromide, calcium chloride or the like; transition metal salts were selected from the group comprising of ferrous chloride, ferric chloride, zinc chloride, copper chloride or the like. Preferably, lithium chloride was used in the present invention.

The present inventors reported the formation of impurity compound 6,6'-(1,4,7,10-tetraazacyclo dodecane-1,7-diyl)bis(2,2-dimethyl-1,3-dioxepan-5-ol) of formula (12) in step a) along with desired compound 2,2-dimethyl-6-(1,4,7,10-tetraazacyclododecan-1-yl)-1,3-dioxepan-5-ol of formula (4). Further the present invention discloses the method for removal of impurity compound of formula (12) by maintaining an optimum pH at 7-10, using a suitable acid. None of the prior art methods disclosed the process for removal of impurity of formula (12) formed in the preparation of compound of formula (4), which is advantageous over prior art as the formation of impurity of formula (12) may carry forward to the next stages, which eventually convert to di-TOBO impurity of formula (8) this may affect the quality of the final compound Gadobutrol of formula (1).

The present invention provides a compound 2,2',2''-(10-((2R,3S)-1,3,4-trihydroxybutan-2-yl)-1,4,7,10-tetraazacyclododecane-1,4,7-triyl)triacetic acid, triammonia salt of formula (2) with a purity greater than 90% which is more advantageous over the prior arts. None of the prior arts disclosed preparation and isolation of ammonium salt of formula (2). The present invention discloses the preparation of ammonium salt of formula (2) in pure form with less impurity levels, which may reduce multiple purification steps in the final gadoburol to avoid the yield loss on large scale. In addition, the present invention discloses the preparation of ammonium salt of formula (2) to control the formation of impurities like di-TOBO of formula (8), and DOTA of formula (13).

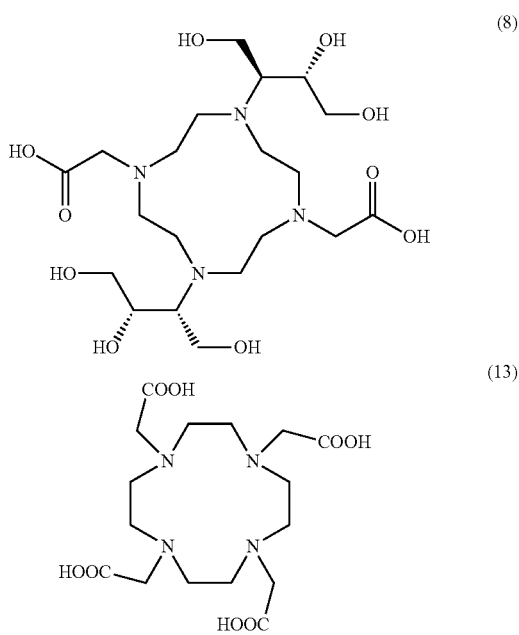

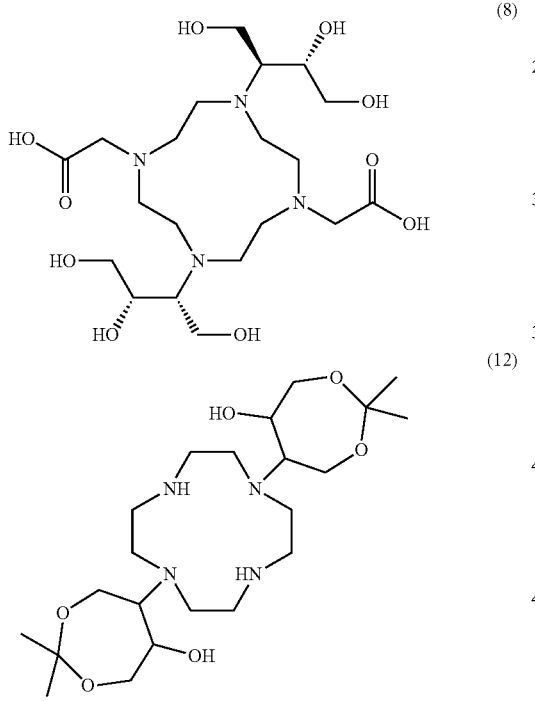

The suitable acid used in the step a) of the present invention may be selected from the group consisting of hydrochloric acid, sulphuric acid, nitric acid, p-toluene sulfonic acid, methane sulphonic acid, oxalic acid, tartaric acid, acetic acid or the like. More preferably, acetic acid was used in the present invention.

In some embodiment, step b) proceeds with preparation of compound 2,2',2''-(10-((2R,3S)-1,3,4-trihydroxybutan-2-yl)-1,4,7,10-tetraazacyclododecane-1,4,7-triyl)triacetic acid, triammonia salt of formula (2) by reacting compound 2,2-dimethyl-6-(1,4,7,10-tetraazacyclododecan-1-yl)-1,3-dioxepan-5-ol of formula (4) with a compound sodium 2-chloroacetate of formula (3) in presence of base at a pH of about 8-12 in a protic solvent. After completion of reaction, the reaction pH was adjusted to 1.0-3.0, using a suitable acid and the product was isolated from a protic solvent after treating with a suitable acidic resin and a base.

The suitable base used in the step b) may be selected from the group comprising of organic and inorganic bases. Organic bases can be selected from the group comprising of pyridine, piperidine, triethylamine, methylamine or the like; inorganic bases can be selected from the group comprising of sodium hydroxide, potassium hydroxide, sodium carbonate, sodium bicarbonate, potassium carbonate, potassium bicarbonate, lithium hydroxide, aqueous ammonia or the like. Preferably, sodium hydroxide and aqueous ammonia were used in the present invention.

The suitable acid used in the step b) may be selected from the group comprising of organic and inorganic acids. Organic acid can be selected from the group comprising of acetic acid, formic acid, p-toluene sulfonic acid, methane sulfonic acid, oxalic acid or the like; inorganic acid can be selected from the group comprising of hydrochloric acid, sulphuric acid, phosphoric acid, nitric acid, perchloric acid or the like. Preferably, hydrochloric acid was used in the present invention.

The suitable acidic resin used for the purification of the ammonia salt intermediate of formula (2) may be selected from a group comprising of Indion 225 Na, Indion 220 Na, Indion 225 H, Indion 225 H (MB), Indion 236, Indion 740, Indion 730, Amberlite IRC 50 or the like. Preferably, Indion 225 H acidic resin was used in the present invention.

In the present invention employing acidic resin is advantageous over the prior art which provides the ammonia salt intermediate of formula (2) in pure form. In addition, it also aids in removal of inorganic impurities like chloride ion. None of the prior arts disclosed the process for the removal of inorganic impurities by employing acidic resin.

In some embodiment, step c) involves preparation of compound 2,2',2"-(10-((2R,3S)-1,3,4-trihydroxybutan-2-yl)-1,4,7,10-tetraazacyclo dodecane-1,4,7-triyl) triacetic acid, gadolinium(III) salt of formula (1) by reacting compound 2,2',2"-(10-((2R,3S)-1,3,4-trihydroxybutan-2-yl)-1,4,7,10-tetraazacyclo dodecane-1,4,7-triyl) triacetic acid, triammonia salt of formula (2) with Gadolinium(III) oxide in a protic solvent, treating with acidic and basic resin.

In some embodiment, advantageously, Indion 225 H resin used in the present invention will assist the removal of ammonia present in the reaction mixture by adjusting pH to 1 to 3.5. Then pH of the reaction mixture was adjusted to 5.0-8.0 by adding a basic resin which aids in stabilizing the Gadolinium complex. None of the prior arts disclosed the present process of preparation of Gadobutrol of formula (1). Prior art methods involve reaction of free acid with gadolinium oxide to form Gadobutrol and adjusting pH of the reaction mass to 6.0 to 7.5 by using inorganic bases like lithium hydroxide, which may lead to contamination of final product with metal content. To avoid the metal content contamination in the final Gadobutrol of formula (1), the present inventors developed a process using acidic and basic resin. The present process is easy to handle on commercial scale and recovery of the resin will reduce the cost of the production at commercial scale. The final Gadobutrol of formula (1) obtained in the present invention contains very low level of total metal content preferably less than 10 ppm. In another aspect the final Gadobutrol of formula (1) contains Iron content less than 2 ppm.

Yet in another embodiment, the present invention provides process for the purification of compound 2,2',2"-(10-((2R,3S)-1,3,4-trihydroxybutan-2-yl)-1,4,7,10-tetraazacyclododecane-1,4,7-triyl) triacetic acid, triammonia salt of formula (2) comprising:
 I. providing a mixture of intermediate of formula (2) in a protic solvent;
 II. adding suitable acidic resin to the reaction mixture;
 III. treating the reaction mixture with suitable base; and
 IV. isolating the pure intermediate of formula (2).

The suitable base used in purifying the compound of formula (2) was selected from a group comprising of sodium hydroxide, ammonium hydroxide, aqueous ammonia, potassium hydroxide or the like. Preferably, aqueous ammonia was used.

Yet, in another embodiment the present invention provides a process for the purification of compound 2,2',2"-(10-((2R,3S)-1,3,4-trihydroxybutan-2-yl)-1,4,7,10-tetraazacyclo dodecane-1,4,7-triyl) triacetic acid, gadolinium (III) salt of formula (1) comprising:
 a) providing a solution of Gadobutrol of formula (1) in a protic solvent;
 b) treating the reaction mixture with acidic and basic resin;
 c) optionally, treating with activated carbon and;
 d) isolating pure Gadobutrol of formula (1)

The suitable protic solvent used for the purification of the intermediate of formula (2) and Gadobutrol of formula (1) may be selected from the group comprising of alcohols, and water. The alcohols may be selected from the group comprising of methanol, ethanol, propanol, isopropanol, butanol, isobutanol, tert-butanol or the like. More preferably water and ethanol were used.

The suitable acidic resin used for the purification of the intermediate of formula (2) and Gadobutrol of formula (1) may be selected from a group comprising of Indion 225 Na, Indion 220 Na, Indion 225 H, Indion 225 H (MB), Indion 236, Indion 740, Indion 730, Amberlite IRC 50 or the like. Preferably, Indion 225 H acidic resin was used.

The suitable basic resin used in purifying Gadobutrol of formula (1) may be selected from a group comprising of Indion 810, Amberlite IRA 67 or the like. Preferably, Indion 810 basic resin was used in the present invention.

The protic solvent used in step a), step b) and step c) of the present invention may be selected from the group comprising of alcohol, water, or the like. The alcohol solvent may be selected from the group comprising of methanol, ethanol, propanol, isopropanol, butanol, iso-butanol or the like. Preferably isopropanol, water, methanol, and ethanol were used in the present invention. The aprotic solvent used in step a) of the present invention may be selected from the group comprising of ethyl acetate, tertiary butyl acetate, ethyl ether, methyl ether, methyl tertbutyl ether, dichloromethane, chloroform, or the like. Preferably dichloromethane was used in the present invention.

Accordingly, in some embodiment the present invention provides an improved process for the preparation of Calcobutrol of formula (1a) and its sodium salt of formula (1b) with purity greater than 98.0% by HPLC.

Calcobutrol of formula (1a) and sodium salt of formula (1b) prepared in the present invention is as shown in scheme 2:

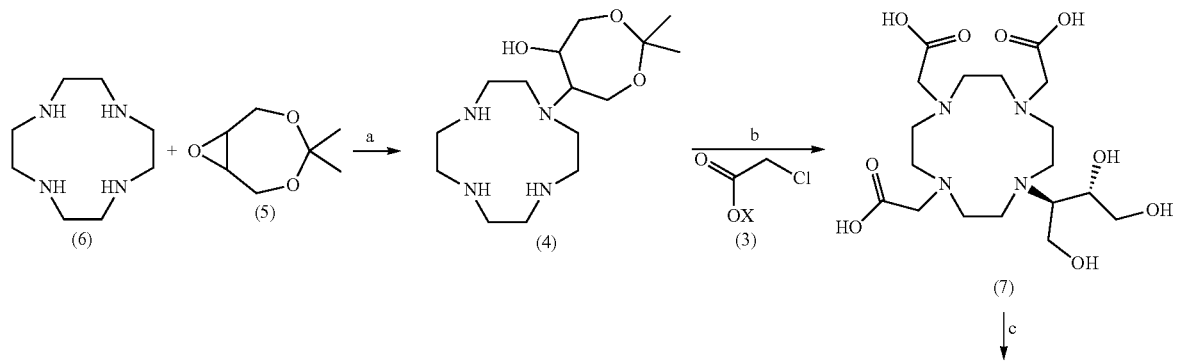

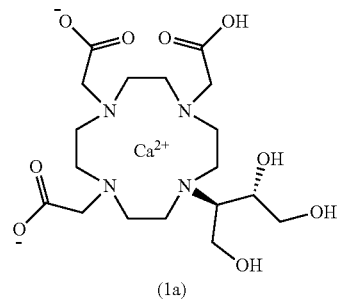

(1a)

wherein, X = H or sodium, potassium or Lithium

Scheme-2: Synthesis of Calcobutrol (1a) and Sodium Salt of Formula (1b)

In some embodiment, step a) proceeds with reacting compound 1,4,7,10-tetraazacyclododecane of formula (6) with compound 4,4-dimethyl-3,5,8-trioxabicyclo [5.1.0] octane of formula (5) to yield compound 2,2-dimethyl-6-(1, 4,7,10-tetraazacyclododecan-1-yl)-1,3-dioxepan-5-ol of formula (4) by in presence of suitable metal salt in a protic solvent and finally, isolating from an protic and aprotic solvents by adjusting the pH to 7-10.

The present inventors reported the formation of impurity compound 6,6'-(1,4,7,10-tetraazacyclo dodecane-1,7-diyl) bis(2,2-dimethyl-1,3-dioxepan-5-ol) of formula (12) in step a) along with desired compound 2,2-dimethyl-6-(1,4,7,10-tetraaza cyclododecan-1-yl)-1,3-dioxepan-5-ol of formula (4). Further the present invention discloses the method for removal of impurity compound of formula (12) by maintaining an optimum pH at 7-10, using a suitable acid. None of the prior arts disclosed the process of removal of impurity of formula (8) formed in the preparation of compound of formula (4), which is advantageous over prior art as the formation of impurity of formula (12) may carry forward to the next stages, which eventually convert into di-TOBO impurity of formula (8) and this may affect the quality of the final compound Sodium salt of Calcobutrol of formula (1a).

The suitable metal salt used in step a) can be selected from the group consisting of alkali metal salts, alkaline earth metal salts, transition metal salts or the like. Alkali metal salts were selected from the group comprising of lithium chloride, sodium chloride, potassium chloride or the like; alkaline earth metal salts were selected from the group comprising of magnesium chloride, magnesium bromide, calcium chloride or the like; transition metal salts were selected from the group comprising of ferrous chloride, ferric chloride, zinc chloride, copper chloride or the like. Preferably, lithium chloride was used in the present invention.

The suitable acid used in the step a) of the present invention was selected from the group consisting of hydrochloric acid, sulphuric acid, nitric acid, p-toluene sulfonic acid, methane sulphonic acid, oxalic acid, tartaric acid, acetic acid or the like. More preferably, acetic acid was used in the present invention.

In some embodiment, step b) proceeds with reacting a compound 2,2-dimethyl-6-(1,4,7,10-tetraazacyclododecan-1-yl)-1,3-dioxepan-5-ol of formula (4) with a compound sodium 2-chloroacetate of formula (3) to provide a compound 2,2',2''-(10-((2R,3S)-1,3,4-trihydroxy butan-2-yl)-1, 4,7,10-tetraazacyclododecane-1,4,7-triyl)triacetic acid of formula (7) in presence of base at a pH of about 7-11 in a protic solvent. Afterwards, the reaction pH was adjusted to 1.0-4.0, using a suitable acid. The compound was isolated from a protic solvent after treating with a suitable acidic resin and a base.

The suitable base used in the step b) may be selected from the group comprising of organic and inorganic bases. Organic bases can be selected from the group comprising of pyridine, piperidine, triethylamine, methylamine or the like; inorganic bases can be selected from the group comprising of sodium hydroxide, potassium hydroxide, sodium carbonate, sodium bicarbonate, potassium carbonate, potassium bicarbonate, lithium hydroxide or the like. Preferably, sodium hydroxide and aqueous ammonia were used in the present invention.

The suitable acid used in the step b) may be selected from the group comprising of organic and inorganic acids. Organic acid can be selected from the group comprising of acetic acid, formic acid, p-toluene sulfonic acid, methane sulfonic acid, oxalic acid or the like; inorganic acid can be selected from the group comprising of hydrochloric acid, sulphuric acid, phosphoric acid, nitric acid, perchloric acid or the like. Preferably, hydrochloric acid was used in the present invention.

The suitable acidic resin used for the purification of the intermediate of formula (2) was selected from a group comprising of Indion 225 Na, Indion 220 Na, Indion 225 H, Indion 225 H (MB), Indion 236, Indion 740, Indion 730, Amberlite IRC 50 or the like. Preferably, Indion 225 H acidic resin was used in the present invention.

In the present invention employing acidic resin is advantageous over the prior arts which provides the intermediate of formula (2) in pure form. In addition, it also aids in removal of inorganic impurities like chloride ion. None of the prior arts disclosed the process for the removal of inorganic impurities by employing acidic resin.

In some embodiment, step c) proceeds with reacting a compound 2,2',2''-(10-((2R,3S)-1,3,4-trihydroxy butan-2-yl)-1,4,7,10-tetraaza cyclododecane-1,4,7-triyl)triacetic acid of formula (7) with calcium hydroxide in a protic solvent to yield calcium 2,2'-(7-(carboxymethyl)-10-((2R, 3S)-1,3,4-trihydroxybutan-2-yl)-1,4,7,10-tetraazacyclododecane-1,4-diyl) diacetate of formula (1a).

In some embodiment, step d) proceeds with purification of Calcobutrol of formula (1a) so formed in step c) may be purified from a mixture of protic and aprotic solvent to yield pure Calcobutrol of formula (1a).

The suitable protic and aprotic solvents used in step a), step b), step c) and step d) were selected from the group comprising of methanol, ethanol, propanol, butanol, tert-butanol, water, acetone, acetonitrile, 1,4-dioxane, diethyl ether, dichloromethane, ethyl acetate, N, N-dimethylformamide, hexane, cyclohexane, toluene, tetrahydrofuran or mixtures thereof. More preferably water, methanol, ethanol, acetone or mixtures thereof were used in the present invention.

Accordingly, in another embodiment the present invention provides an improved process for the preparation of sodium salt of Calcobutrol (1b) with purity greater than 98.0%, prepared in the present invention is as shown in scheme 3:

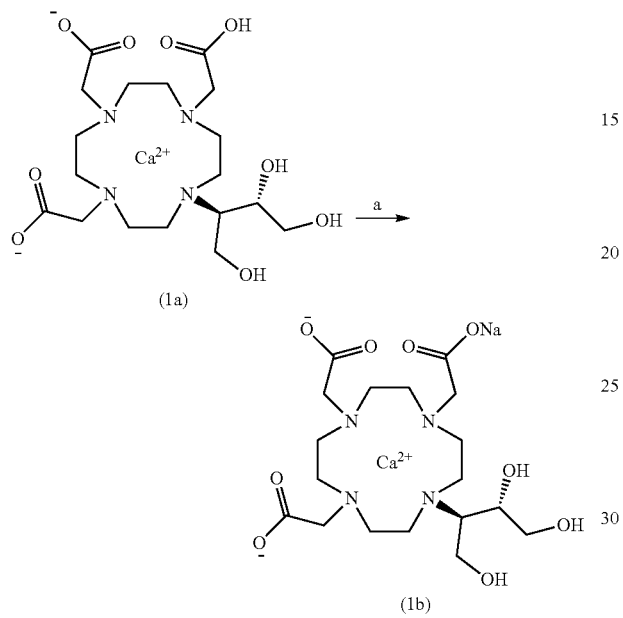

Scheme-3: Synthesis of Sodium Salt of Calcobutrol (1b)

Step e) involves preparation of sodium salt of Calcobutrol of formula (1b) involves reacting Calcobutrol of formula (1a) with sodium hydroxide in a protic solvent and isolated a pure sodium salt of Calcobutrol of formula (1b) from a mixture of protic and aprotic solvent.

The suitable protic and aprotic solvents used in step e) for the preparation of sodium salt of Calcobutrol of formula (1b) were selected from the group comprising of methanol, ethanol, propanol, butanol, tert-butanol, water, acetone, acetonitrile, 1,4-dioxane, diethyl ether, dichloromethane, ethyl acetate, N, N-dimethylformamide, hexane, cyclohexane, toluene, tetrahydrofuran or mixtures thereof. More preferably water, methanol, ethanol, acetone or mixtures thereof were used in the present invention.

In one embodiment the present invention provides a process for the purification of compound of Calcobutrol of formula (1a) comprising:
I. providing a solution of Calcobutrol of formula (1a) in a protic solvent or mixture thereof,
II. heating the reaction mixture;
III. optionally, treating the reaction mixture with charcoal; and
IV. isolating the pure Calcobutrol of formula (1a).

The suitable protic solvent used for the purification of the Calcobutrol of formula (1a) may be selected from the group comprising of alcohols, and water. The alcohols may be selected from the group comprising of methanol, ethanol, propanol, isopropanol, butanol, isobutanol, tert-butanol or the like. More preferably methanol and ethanol were used in the present invention.

In one embodiment the impurities (8), (9) were removed by simple purification processes of washing with suitable protic solvents, wherein the impurities are precipitated and separated by filtration to get pure Calcobutrol of formula (1a).

In some embodiment, the present invention provides 2,2',2''-(10-((2R,3S)-1,3,4-trihydroxybutan-2-yl)-1,4,7,10-tetraazacyclo dodecane-1,4,7-triyl) triacetic acid, gadolinium (III) salt of formula (1) having purity greater than 99.0%.

The Gadobutrol of formula (1) obtained in the present invention is having an Iron metal content less than 5 ppm, which forms another embodiment of the present invention. None of the prior arts mentioned about iron metal content embedded in Gadobutrol of formula (1). If the iron metal content is more than 5 ppm it may lead to decomposition of Gadobutrol of formula (1) by replacing gadolinium metal with iron metal.

In another embodiment the Gadobutrol of formula (1) obtained in the present invention is having impurities (8), (9), (10) and (11) less than 1.0% (w/w) and more preferably less than 0.5% (w/w).

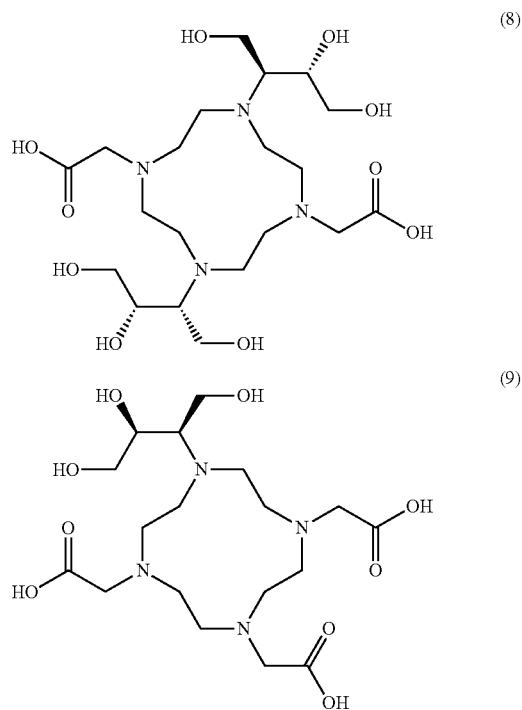

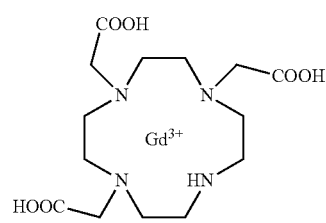

-continued

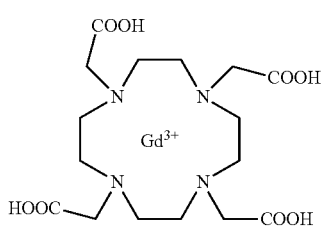
(11)

Another embodiment, the present invention provides Gadobutrol with free gadolinium content less than 50 ppm, more preferably less than 20 ppm and still more preferably less than 10 ppm.

In another embodiment the present invention provides Gadobutrol of formula (1) having characteristic X-Ray powder diffraction is as shown in FIG. 1, may have 2(θ) values (±0.2) as tabulated in Table-1 below:

TABLE 1

| 2 Theta (2θ°) deg. | Relative Intensity (%) |
|---|---|
| 8.04 | 46.4 |
| 10 | 17.5 |
| 10.5 | 14.0 |
| 11.33 | 100 |
| 11.86 | 54.5 |
| 12.67 | 26.1 |
| 13.26 | 12.3 |
| 13.62 | 13.8 |
| 14.19 | 19.2 |
| 14.99 | 20.8 |
| 16.2 | 11.7 |
| 17.33 | 8.80 |
| 18.42 | 17.3 |
| 18.86 | 8.00 |
| 21.11 | 13.7 |
| 21.58 | 15.0 |
| 24.37 | 14.5 |
| 24.72 | 15.3 |
| 25.07 | 9.40 |
| 26.07 | 13.4 |
| 26.77 | 12.0 |
| 28.31 | 9.10 |
| 28.64 | 10.7 |
| 29.77 | 14.6 |
| 30.7 | 12.3 |
| 32.35 | 9.90 |
| 33.66 | 13.5 |
| 36.25 | 12.2 |
| 38.45 | 7.90 |
| 43.11 | 8.80 |

In yet another embodiment the present invention provides Calcobutrol of formula (1a) and its sodium salt of formula (1b) having purity greater than 98.0%.

In another embodiment the present invention provides crystalline form of Calcobutrol of formula (1a) having characteristic X-Ray powder diffraction is as shown in FIG. 2, may have 2(θ) values (±0.2) as tabulated in Table 2 below:

TABLE 2

| S. No | 2theta (θ) deg. | Relative Intensity (%) |
|---|---|---|
| 1 | 3.04 | 10.4 |
| 2 | 5.52 | 10.7 |
| 3 | 8.23 | 22.9 |
| 4 | 8.64 | 33.5 |
| 5 | 9.27 | 100 |
| 6 | 9.66 | 37.0 |

TABLE 2-continued

| S. No | 2theta (θ) deg. | Relative Intensity (%) |
|---|---|---|
| 7 | 10.82 | 18.2 |
| 8 | 11.43 | 31.7 |
| 9 | 12.71 | 21.4 |
| 10 | 12.53 | 15.8 |
| 11 | 13.17 | 12.4 |
| 12 | 14.56 | 13.8 |
| 13 | 20.36 | 15.1 |
| 14 | 22.08 | 10.3 |
| 15 | 22.96 | 12.9 |
| 16 | 23.6 | 12.2 |
| 17 | 23.92 | 11.2 |
| 18 | 25.3 | 12.1 |
| 19 | 26.0 | 10.4 |
| 20 | 26.72 | 10.8 |
| 21 | 27.97 | 12.8 |
| 22 | 28.69 | 10.2 |
| 23 | 32.48 | 11.4 |
| 24 | 38.71 | 10.6 |

In some embodiment Calcobutrol of formula (1a) and its sodium salt of formula (1b) obtained in the present invention were having total impurities less than 2% (w/w) and more preferably less than 1% (w/w).

In some embodiment Calcobutrol of formula (1a) and its sodium salt formula (1b) obtained in the present invention having Calcium-DOTA impurity (14) less than 2%, preferably less than 1%, and Calcium di-TOBO impurity of formula (15) is less than 0.5% (w/w) and calcium triacid impurity of formula (16) is less than 0.5% (w/w).

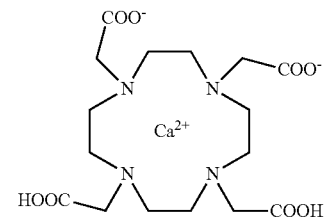
(14)

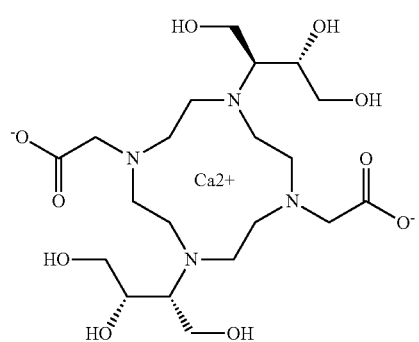
(15)

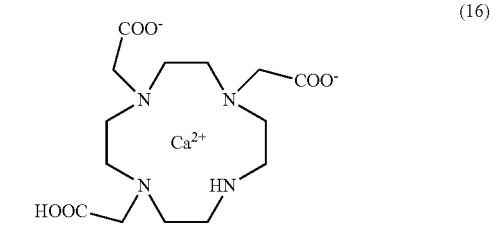
(16)

In another embodiment the present invention provides amorphous form of Calcobutrol sodium of formula (1b).

In another embodiment the present invention provides Sodium salt of Calcobutrol of formula (1b) having characteristic X-Ray powder diffraction is as shown in FIG. 3.

The following examples further illustrate the present invention but should not be construed in any way as to limit its scope.

EXAMPLES

Example-1: Preparation of 2,2-dimethyl-6-(1,4,7,10-tetraazacyclododecan-1-yl)-1,3-dioxepan-5-ol of formula (4)

92.0 g of 4,4-dimethyl-3,5,8-trioxabicyclo [5.1.0] octane (5) was added to a reaction mixture of 100 g of 1,4,7,10-tetraazacyclododecane (6) in 200 mL of isopropyl alcohol at 25-30° C. To this solution 25 g of lithium chloride was added and heated to 80-85° C. for 23-24 hrs. On completion of reaction, the reaction mass was distilled off completely under vacuum. 500 mL water was added to the crude and stirred. The pH of the reaction mixture was adjusted to 7-10.0 by adding 57.0 mL of acetic acid. The reaction mixture was diluted with 900 mL of dichloromethane and stirred at 25-30° C. The phases were separated, the aqueous layer was treated with 50% sodium hydroxide and stirred for 10-15 mins. The reaction mixture was diluted with 600 mL of the dichloromethane and phases were separated. The organic layer was dried over sodium sulphate, filtered and the filtrate so obtained was distilled off under vacuum to obtain solid 2,2-dimethyl-6-(1,4,7,10-tetraazacyclododecan-1-yl)-1,3-dioxepan-5-ol of formula (4). Yield: 78%; Purity: 86.96%.

Example-2: Alternative Process for the Preparation of 2,2-dimethyl-6-(1,4,7,10-tetraazacyclododecan-1-yl)-1,3-dioxepan-5-ol of formula (4)

92.0 g of 4,4-dimethyl-3,5,8-trioxabicyclo [5.1.0] octane (5) was added to a reaction mixture of 100 g of 1,4,7,10-tetraazacyclododecane (6) in 200 mL of isopropyl alcohol at 25-30° C. To this solution 25 g of lithium chloride was added and heated to 80-85° C. for 23-24 hrs. On completion of reaction, the reaction mass was distilled off completely under vacuum. 500 mL water was added to the crude and stirred. The pH of the reaction mixture was adjusted to 7-8.5 by adding 57.0 mL of acetic acid. The reaction mixture was diluted with 900 mL of dichloromethane and stirred at 25-30° C. The phases were separated, the aqueous layer was treated with 50% sodium hydroxide and stirred for 10-15 mins. The reaction mixture was diluted with 600 mL of the dichloromethane and phases were separated. The organic layer was dried over sodium sulphate, filtered and the filtrate so obtained was distilled off under vacuum to obtain solid 2,2-dimethyl-6-(1,4,7,10-tetraazacyclododecan-1-yl)-1,3-dioxepan-5-ol of formula (4). Yield: 78%; Purity: 86.96%.

Example 3: Preparation of 2,2',2"-(10-((2R,3S)-1,3,4-trihydroxybutan-2-yl)-1,4,7,10-tetraaza cyclododecane-1,4,7-triyl) Triacetic Acid, Triammonia Salt of Formula (2)

100 g of 2,2-dimethyl-6-(1,4,7,10-tetraazacyclododecan-1-yl)-1,3-dioxepan-5-ol (4) was dissolved in 300 mL of water. 138 g of sodium chloroacetate (3) was added to the reaction mass and heated to 65-70° C. The pH of the reaction mass was adjusted to 8-12 with 100 mL of sodium hydroxide and maintained for 12-14 hrs at 65-70° C. On completion of reaction, the reaction mass was cooled to 10-15° C. and pH was adjusted to 1.0-4.0 by adding 115 mL of conc. hydrochloric acid. The reaction mixture was distilled off at below 50° C. To the concentrated reaction mass, 200 mL methanol was added and stirred at 25-30° C., then filtered. The filtrate was diluted with 1000 mL water and 3000 mL of acidic resin was added and stirred for 30-45 min at 25-30° C. The reaction mass was filtered and washed with water. To the resin 1250 mL of 20-25% aq. ammonia was added and maintained the reaction mass at 40-45° C. for 1-2 hrs. The reaction mass was filtered and washed with water. The filtrate was distilled off to obtain 2,2',2"-(10-((2R,3S)-1,3,4-trihydroxybutan-2-yl)-1,4,7,10-tetraazacyclododecane-1,4,7-triyl) triacetic acid, triammonia salt of formula (2). Yield: 82%, Purity: 93.68%.

Example 4: Preparation of 2,2',2"-(10-((2R,3S)-1,3,4-trihydroxybutan-2-yl)-1,4,7,10-tetraaza Cyclododecane-1,4,7-Triyl) Triacetic Acid, Triammonia Salt of Formula (2)

100 g of 2,2-dimethyl-6-(1,4,7,10-tetraazacyclododecan-1-yl)-1,3-dioxepan-5-ol (4) was dissolved in 300 mL of water. 120 g of chloroacetic acid was added to the reaction mass and heated to 65-70° C. The pH of the reaction mass was adjusted to 8-12 with 100 mL of sodium hydroxide and maintained for 12-14 hrs at 65-70° C. On completion of reaction, the reaction mass was cooled to 10-15° C. and pH was adjusted to 1.0-4.0 by adding 115 mL of conc. hydrochloric acid. The reaction mixture was distilled off at below 50° C. To the concentrated reaction mass, 200 mL methanol was added and stirred at 25-30° C., then filtered. The filtrate was diluted with 1000 mL water and 5000 mL of acidic resin was added and stirred for 30-45 min at 25-30° C. The reaction mass was filtered and washed with water. To the resin 1250 mL of 20-25% aq. ammonia was added and maintained the reaction mass at 40-45° C. for 1-2 hrs. The reaction mass was filtered and washed with water. The filtrate was distilled off to obtain 2,2',2"-(10-((2R,3S)-1,3,4-trihydroxybutan-2-yl)-1,4,7,10-tetraazacyclododecane-1,4,7-triyl) triacetic acid, triammonia salt of formula (2). Yield: 82%, Purity: 93.68%.

Example 5: Preparation of 2,2',2"-(10-((2R,3S)-1,3,4-trihydroxybutan-2-yl)-1,4,7,10-tetraazacyclododecane-1,4,7-triyl) Triacetic Acid, Gadolinium Salt (1)

100 g of 2,2',2"-(10-((2R,3S)-1,3,4-trihydroxybutan-2-yl)-1,4,7,10-tetraaza cyclododecane-1,4,7-triyl) triacetic acid, triammonia salt (2) was added to 500 mL of water. 42 g of gadolinium oxide was added and the reaction mixture was heated to 95-100° C. for 6-7 hrs. Upon completion of reaction, the reaction mixture was filtered through Hyflo bed. To the filtrate 150 mL of Indion 225 H resin was added and pH adjusted to about 1.0 to 3.5 and stirred at 25-30° C. for 25-30 min. The reaction mass was filtered and 150 mL of basic resin was added to the filtrate. The reaction mass pH was adjusted to about 5.0 to 8.0. The reaction mixture was stirred at 25-30° C. and filtered. To the filtrate 10 g of activated carbon was added and the mixture was stirred. The activated carbon is filtered off through Hyflo and the solvent distilled off under vacuum. To the concentrated reaction mass 50 mL of water was added and the reaction mass was heated to 75-80° C. 700 mL of ethanol was added to the reaction mass under at 75-80° C. for 5-6 hrs. Further reaction mass was cooled to 25-30° C. and maintained and filtered. The solid so obtained was dried under vacuum to furnish titled 2,2',2"-(10-((2R,3S)-1,3,4-trihydroxybutan-2-yl)-1,4,7,10-tetraazacyclo dodecane-1,4,7-triyl) triacetic acid, gadolinium salt of formula (1) Yield: 92%, Purity: 99.9%.

Purification of 2,2',2"-(10-((2R,3S)-1,3,4-trihydroxybutan-2-yl)-1,4,7,10-tetraazacyclododecane-1,4,7-triyl) Triacetic Acid, Gadolinium Salt (1)

100 g of compound (1) was dissolved in 500 mL of water and the pH was adjusted to about 3.0 to 4.0 using 100 mL of Indion 225 H resin. The reaction mixture was stirred at 25-30° C. and filtered. 100 mL of basic resin was added to the filtrate and pH adjusted to about 7.0-10.0. The reaction mixture was stirred at 25-30° C. for 20-30 min and filtered. 5 g of activated carbon was then added to the filtrate, stirred and filtered through Hyflo. The filtrate was further passed through 0.2-micron filter. The filtrate so obtained was distilled off the solvent at below 60° C. To the concentrated reaction mass 50 mL of water was added and the reaction mass was heated to 70-80° C. 850 mL of ethanol was then added to the reaction mass at 70-80° C. Further reaction mass was cooled to 25-30° C. and the obtained solid was filtered and dried under vacuum below 50° C. to obtain pure 2,2',2"-(10-((2R,3S)-1,3,4-trihydroxybutan-2-yl)-1,4,7,10-tetraazacyclododecane-1,4,7-triyl) triacetic acid, gadolinium salt of formula (1). Yield: 87%, Purity: 99.95%, moisture content: 2.41%, Iron content: less than 1 ppm.

Example 6: Preparation of 2,2',2"-(10-((2R,3S)-1,3,4-trihydroxybutan-2-yl)-1,4,7,10-tetraaza cyclododecane-1,4,7-triyl) Triacetic Acid (7)

100 g of 2,2-dimethyl-6-(1,4,7,10-tetraazacyclododecan-1-yl)-1,3-dioxepan-5-ol (4) was dissolved in 300 mL of water. 138.2 g of sodium chloroacetate (3) was added to the reaction mass and heated to 65-70° C. The pH of the reaction mass was adjusted to 7.0-10.0 using 100 mL of sodium hydroxide at 65-70° C. On completion of reaction, the reaction mass was cooled to 10-15° C. and pH of the reaction mass was adjusted to 1.0-4.0 with 130 mL of conc. hydrochloric acid. The solvent of the reaction mass was distilled off at below 50° C. The concentrated reaction mass was diluted with 200 mL methanol and reaction continued at 25-30° C. The reaction mass was then filtered to remove inorganic salts. The filtrate was diluted with 1000 mL water, 3000 mL of Indion 225 H resin was added and stirred for 30-45 min at 25-30° C. The resin was filtered and washed with water. To the resin 1250 mL of 20-25% aqueous ammonia was added at 40-45° C. for 30-45 minutes. The reaction mass was filtered and washed with water; water was distilled off completely at below 60° C. The reaction mass was cooled to 25-30° C. and the pH was adjusted to 3.5-4.0 by adding Indion 225 H resin. The resin was again filtered, and the filtrate distilled off to obtain titled 2,2',2"-(10-((2R,3S)-1,3,4-trihydroxybutan-2-yl)-1,4,7,10-tetraaza cyclododecane-1,4,7-triyl) triacetic acid of formula (7). Yield: 85%.

Example 7: Preparation of Calcium 2,2'-(7-(carboxymethyl)-10-((2R,3S)-1,3,4-trihydroxy butan-2-yl)-1,4,7,10-tetraazacyclododecane-1,4-diyl) diacetate (1a)

100 g of 2,2',2"-(10-((2R,3S)-1,3,4-trihydroxybutan-2-yl)-1,4,7,10-tetraazacyclo dodecane-1,4,7-triyl) triacetic acid (7) was dissolved in 500 mL water. 16.5 g of calcium hydroxide was added to the reaction mass and heated to 55-60° C. Upon completion of reaction, the crude was cooled and 10 g of activated carbon was added and then filtered through Hyflo. Water was distilled off from filtrate and the obtained crude was washed with methanol and acetone. The crude was diluted with 100 mL of methanol and heated. The reaction mass was then cooled to 25-30° C. and 500 mL acetone was added. The solid so obtained was filtered and dried under vacuum below 50° C. To this, ethanol was added and heated to 75-80° C. Then reaction mass was filtered and dried under vacuum below 50° C. Again, 5 volumes of methanol were added and heated to 60-65° C. Then reaction mass was cooled, filtered and dried under 50-55° C. to obtained pure calcium 2,2'-(7-(carboxymethyl)-10-((2R,3S)-1,3,4-trihydroxy butan-2-yl)-1,4,7,10-tetraazacyclododecane-1,4-diyl) diacetate formula (1a). Yield: 90.0%, Purity 99.1% (HPLC).

Example 8: Preparation of Calcium Sodium 2,2',2"-(10-((2R,3S)-1,3,4-trihydroxybutan-2-yl)-1,4,7,10-tetraazacyclododecane-1,4,7-triyl) Triacetate (1b)

100 g of calcium 2,2'-(7-(carboxymethyl)-10-((2R,3S)-1,3,4-trihydroxybutan-2-yl)-1,4,7,10-tetraazacyclododecane-1,4-diyl) diacetate of formula (1a) was added to 500 mL of water at 25-30° C. The pH of the reaction solution was adjusted to 7.0-11 with 10% sodium hydroxide solution. 10 g of activate carbon was added to the reaction mass and filtered through 0.2 mm micron filter. The filtrate was distilled off and washed with methanol at below 55° C. The crude obtained was diluted with 100 mL of methanol and heated to 55° C. The reaction mass was cooled to 25-30° C. and 500 mL of acetone was added to the reaction and filtered. The obtained solid was washed with acetone and dried under vacuum below 55° C. to get sodium salt calcium 2,2'-(7-(carboxymethyl)-10-((2R,3S)-1,3,4-trihydroxybutan-2-yl)-1,4,7,10-tetraaza cyclododecane-1,4-diyl) diacetate of formula (1b). Yield: 95%, Purity: 98.7% (HPLC).

While the present disclosure has been illustrated and described with respect to a particular embodiment thereof, it should be appreciated by those of ordinary skill in the art that various modifications to this disclosure may be made without departing from the spirit and scope of the present disclosure.

What is claimed is:

1. An improved process for the preparation of Gadobutrol of formula (1) with purity greater than 99.0%,

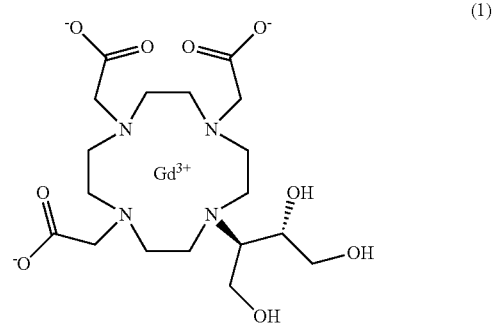

the process consisting essentially of the steps:
a) reacting 1,4,7,10-tetraazacyclododecane of formula (6)

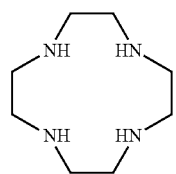

(6)

with 4,4-dimethyl-3,5,8-trioxabicyclo [5.1.0] octane of formula (5)

(5)

In presence of metal salt to obtain 2,2-dimethyl-6-(1,4,7,10-tetraazacyclododecan-1-yl)-1,3-dioxepan-5-ol of formula (4);

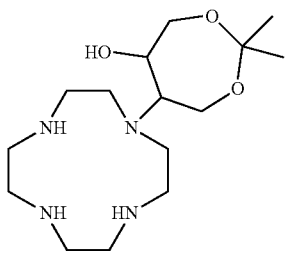

(4)

b) reacting 2,2-dimethyl-6-(1,4,7,10-tetraazacyclododecan-1-yl)-1,3-dioxepan-5-ol of the formula (4) with chloroacetic acid or its salts of formula (3)

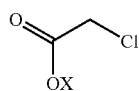

(3)

Wherein X=H or Sodium, potassium or Lithium
and a base and purifying by adding an acidic or a basic resin and adding ammonia thereby obtaining 2,2',2"-(10-((2R,3S)-1,3,4-trihydroxybutan-2-yl)-1,4,7,10-tetraazacyclododecane-1,4,7-triyl) triacetic acid, triammonia salt of formula (2);

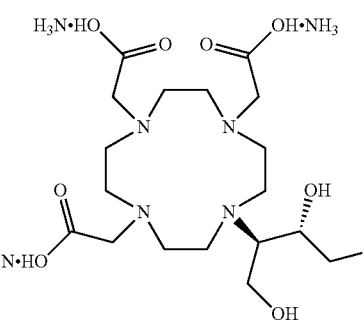

(2)

c) reacting 2,2',2"-(10-((2R,3S)-1,3,4-trihydroxybutan-2-yl)-1,4,7,10-tetraaza cyclododecane-1,4,7-triyl) triacetic acid, triammonia salt of formula (2) with gadolinium (III) oxide to yield the Gadobutrol of the formula (1); and d) purifying the Gadobutrol of the formula (1) by treating with acidic resin and basic resins.

2. The process as claimed in claim 1, wherein the metal salt employed in step a) is selected from the group consisting of lithium chloride, lithium bromide, sodium chloride, potassium chloride; magnesium chloride, magnesium bromide, calcium chloride; ferrous chloride, ferric chloride, zinc chloride and copper chloride.

3. The process as claimed in claim 1, wherein the base employed in the step b) is selected from the group consisting of sodium hydroxide, potassium hydroxide, sodium carbonate, sodium bicarbonate, potassium carbonate, potassium bicarbonate, lithium hydroxide, and aqueous ammonia or mixtures thereof.

4. The process as claimed in claim 1, wherein purification of Gadobutrol of formula (1) consists essentially of the steps:
   a) providing a solution of Gadobutrol of formula (1) in a protic solvent;
   b) treating the reaction mixture with acidic and basic resin;
   c) optionally, treating with activated carbon; and
   d) isolating pure Gadobutrol of formula (1).

5. The process as claimed in claim 4, wherein protic solvent employed is selected from the group consisting of water, methanol, ethanol, propanol, isopropanol, butanol, iso butanol, and tert-butanol or mixture thereof.

* * * * *